United States Patent [19]

Opitz et al.

[11] Patent Number: 4,597,392
[45] Date of Patent: Jul. 1, 1986

[54] ARRANGEMENT FOR MEASURING DIFFUSING PARTICLES

[75] Inventors: Norbert Opitz, Schwerte; Dietrich W. Lübbers, Dortmund, both of Fed. Rep. of Germany

[73] Assignee: Max Planck Gesellschaft, Munich, Fed. Rep. of Germany

[21] Appl. No.: 597,105

[22] Filed: Apr. 2, 1984

[30] Foreign Application Priority Data

Apr. 12, 1983 [DE] Fed. Rep. of Germany ....... 3313047

[51] Int. Cl.[4] ................................................. A61B 5/00
[52] U.S. Cl. ................................. 128/637; 128/633; 128/634; 128/635; 128/636; 128/665; 128/666; 128/745; 351/221; 356/38; 356/39; 356/317; 356/318
[58] Field of Search ............... 128/634, 635, 636, 637, 128/633, 665, 666, 745; 351/221; 356/38, 39, 317, 318

[56] References Cited

U.S. PATENT DOCUMENTS

| 3,893,444 | 7/1975 | Fatt | 128/635 |
|---|---|---|---|
| 4,003,707 | 1/1977 | Lubbers et al. | 128/633 |
| 4,014,321 | 3/1977 | March | 128/633 |
| 4,041,932 | 8/1977 | Fostick | 128/633 |
| 4,269,516 | 5/1981 | Lubbers et al. | 356/39 |
| 4,306,877 | 12/1981 | Lubbers | 128/633 |
| 4,350,163 | 9/1982 | Ford et al. | 128/745 |

Primary Examiner—Curtis R. Davis
Attorney, Agent, or Firm—Michael J. Striker

[57] ABSTRACT

An arrangement for measuring diffusing particles has at least one monochromatic radiation source and a light measuring device, as well as at least one material limited particle-permeable indicator chamber provided with an optical fluorescent indicator which is optically changeable by the particles to be measured, and a carrier body having a surface which is arranged to face an eyelid and has depressions in which the indicator chambers are arranged.

10 Claims, 7 Drawing Figures

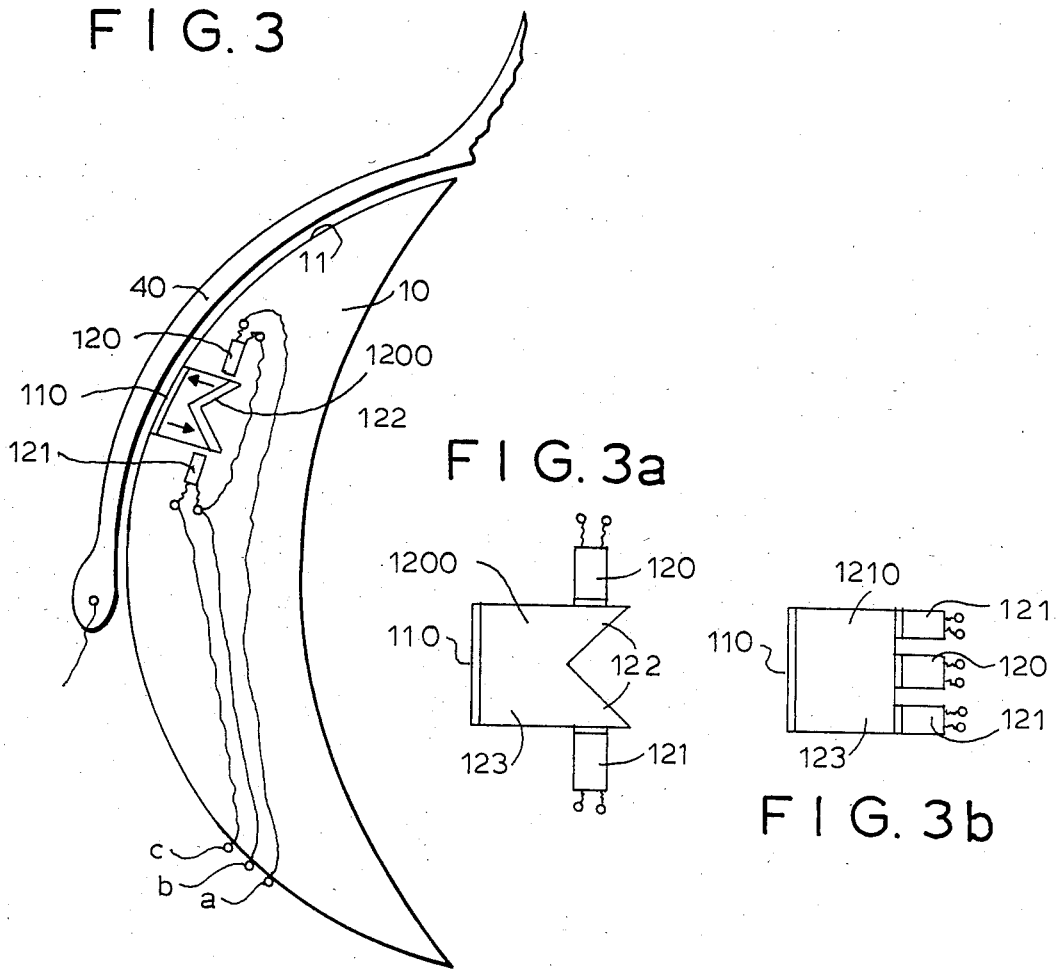

ARRANGEMENT FOR MEASURING DIFFUSING PARTICLES

BACKGROUND OF THE INVENTION

The present invention relates to an arrangement for measuring diffusing particles. More particularly, it relates to an arrangement for measuring diffusing particles, which has at least one monochromatic radiation source and a light measuring device as well as at least one material-limited indicator chamber which is permeable by particles to be measured and is provided with an optical fluorescence indicator which is optically changeable by the particles.

Arrangements of the above-mentioned general type are known in the art. The known arrangements are used for example for measurements of blood component oxygen and its partial pressure pO2 or carbon dioxide and its partial pressure pCO2 invasibly or noninvasibly. For this purpose the indicator chamber which is permeable by the particles to be measured, known shortly as optode, is brought into operative communication with the object to be measured and the change in the measuring light is measured by the optode. One of such arrangements is disclosed, for example, in the U.S. Pat. No. 3,769,961. In the arrangement in accordance with this patent the electrodes which are arranged on a contact lens formed as an electrode carrier measure blood components, such as for example oxygen or carbon dioxide on an eyelid.

In this manner a noninvasive measurement of these blood components is possible, since on the lid mucous membrane or the conjunctiva these blood components have approximately arterial value, or differ from it only by a constant factor.

The electrodes which in the known arrangement are used for measurements have as all electrodes an aging and must be frequently subjected to observations with considerable cost. Moreover, the wire lines for the electrodes must be guided on the contact lens that leads to undesirably affecting of the patients. Furthermore, the miniaturization of electrodes is possible only to a limited extent. Also, other particle types such as for example metabolism products from the metabolism of the eye or other particles such as for example cations or anions lie at this measuring location. They cannot, however, be measured since there are no suitable sensors.

SUMMARY OF THE INVENTION

Accordingly, it is an object of the present invention to provide an arrangement for measuring diffusing particles which avoids the disadvantages of the prior art.

In keeping with these objects and with others which will become apparent hereinafter, one feature of the present invention resides, briefly stated, in an arrangement for measuring diffusing particles, which has a carrier body provided at its surface facing toward a lid with depressions, and indicator chambers (optodes) are arranged in these depressions.

When the arrangement is designed in accordance with the present invention it is possible to for example simultaneously measure several particle types in a contactless manner, in that the optodes arranged on the carrier body are irradiated directly after lifting of the eyelid or through the eyelid with a testing light, and then the measuring light going out of the optodes and its change is used for indicating purposes. Thereby here a noninvasive method for measuring of the pH value takes place since protones also with approximately arterial value are measured on the eyelid. Because of the robust state of the optodes, the arrangement is non problematic in handling and its compatibility for the patients is very good as the known compatibility of the contact lenses. Since moreover, optical indicators are provided for a whole range of diffusing particles, the measuring region is considerably increased as compared with the measurements by electrodes. For example, with the aid of optodes also the glucose concentration on the lid can be measured.

An especially fine and at the same time intensive irradiation of the optodes is obtained when, in accordance with another feature of the present invention, light conductors are provided inside the carrier body and lead from one or several coupling surfaces arranged at the edge of the carrier body to the optodes.

If in special measuring conditions the utilization of wire conduits is not desirable, then, in accordance with a further feature of the present invention, a monochromatic radiation source, for example a light diode and the associated radiation receiver can be arranged in the carrier body. The irradiation of the optodes and the measurement of the radiation changes take place directly by the optodes. Several such arrangements can also be used.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 3 is a view showing an arrangement for measuring diffusing particles in accordance with a further embodiment of the present invention; and FIGS. 3A and 3B are views showing modifications of the third embodiment of the invention.

DESCRIPTION OF PREFERRED EMBODIMENTS

Figures 1, 1A:
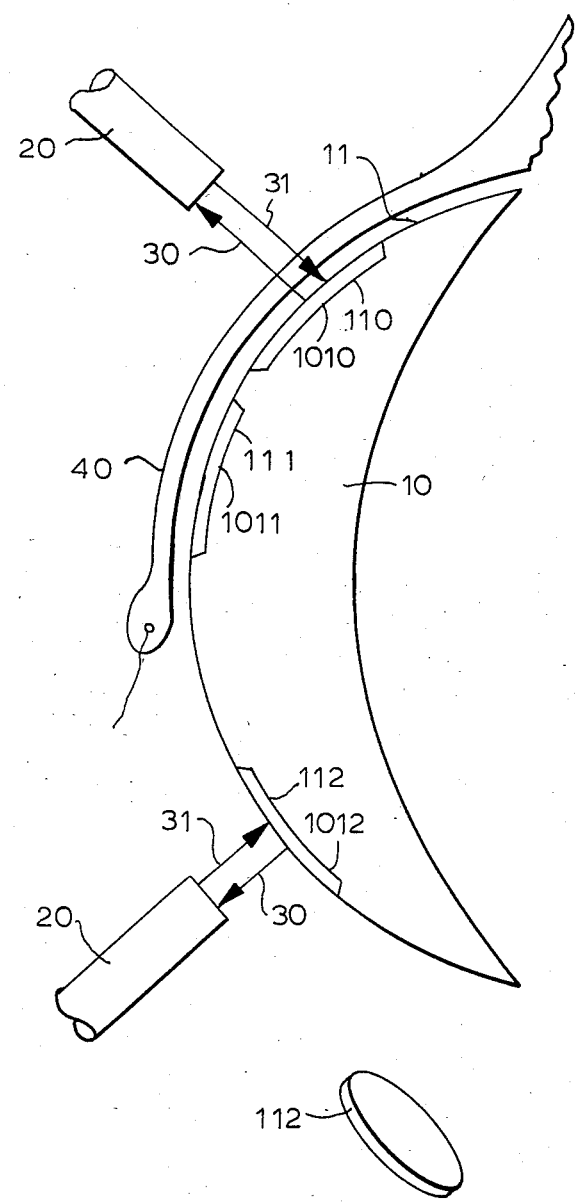
FIG. 1 is a view showing an arrangement for measuring diffusing particles in accordance with a first embodiment of the present invention.
FIG. 1A is a perspective view showing an optode of the inventive arrangement.

An arrangement for measuring diffusing particles shown in FIG. 1 has a carrier body which is identified with reference numeral 10. The carrier body has a surface 11 which is arranged to lie on an eyelid and provided with depressions 1010, 1011 . . . The depressions have a rear side which can be formed reflective. Optodes 110, 111 . . . are arranged in the depressions 1010, 1011 . . . Such optodes are composed, for example, of synthetic plastic foil with indicators arranged in it, as shown in FIG. 1. During irradiation with light they produce a predetermined fluorescent light with a wavelength depending upon the indicator. The fluorescent light or "measuring light" 30 has a different color than a testing light 31. The measuring light 30 as well as the testing light 31 in FIG. 1 are transported by a light conductor 20 which can have several fibers. A known optical means can easily separate it from the measuring light and detect. The device required for this is known in the art and therefore not shown here.

The indicator which produces this fluorescent light is, in turn, influenced by a type of the particles to be measured, for example oxygen which goes from the inner surface of an eyelid 40 and is in a diffusing equilibrium with the capillary oxygen in the mucous membrane of the eyelid, and changes its fluorescent light emission in correspondence with the concentration of the oxygen.

The measurements of $pO_2$ and $pCO_2$ takes place through the eyelid with the aid of the optodes 110, 111 ..., and therefore there are no distortions by the atmosphere. This is possible since the fluorescent light of the indicator can be well filtered from the reflected radiation.

Furthermore, the optodes can be produced without difficulties from bio-compatible materials, so that neither toxic nor contaminating processes are released by the measurement. By optical disengagement of the optodes with the aid of a reflecting or absorbing layers the possible irradiation in the retina during the measurements can be excluded.

The thus measured intensity of the fluorescent light is multiplied by a corrective factor which is determined by calibration. The deviation of the partial pressure from the arterial pressures can be eliminated by a further correction.

For special measurement tasks an optode 112 can be arranged in an open lid gap. Furthermore, several optodes can be provided in the arrangement, particularly for simultaneous measurements of several types of particles or physical parameters, such as for example, the oxygen concentration, the $CO_2$ partial pressure, the pH value, the glucose concentration, the temperature and the like.

Figure 2:
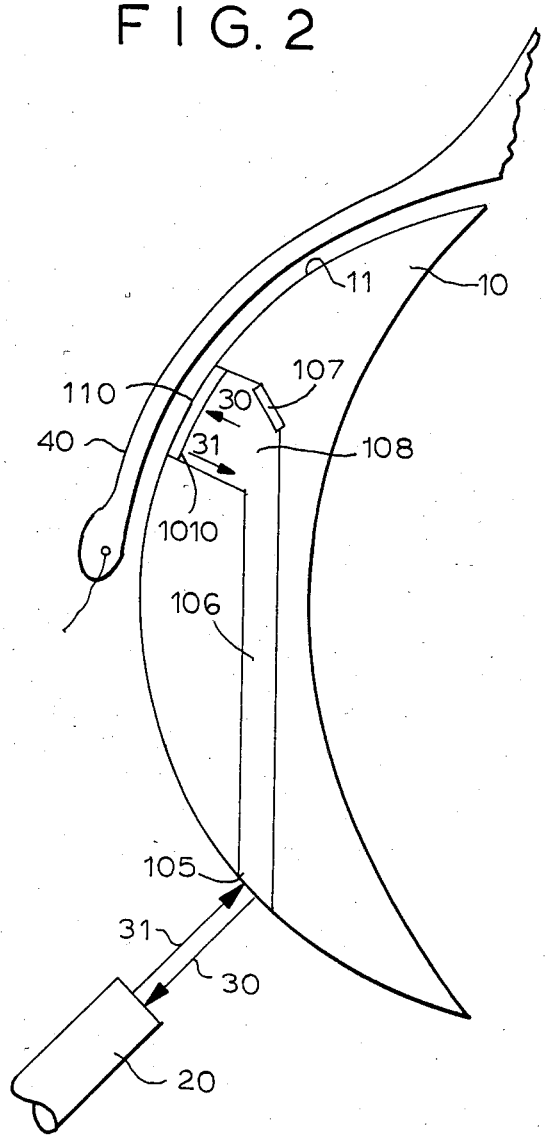
FIG. 2 shows an arrangement for measuring diffusing particles in accordance with a second embodiment of the present invention.

The arrangement for measuring diffusing particles shown in FIG. 2 is used when the $pO_2$ value, the pH value, or the $pCO_2$ value is measured with an open lid and therefore the irradiation does not have to take place through the eyelid.

For this purpose, the depression 1010 is arranged at an edge of the carrier body 10 so far that the lid 40 permenantly covers this optode. The light conductor which transports the testing light 31 and the measuring light 30 irradiates a coupling surface 105 which is an end surface of a light conduit 106 conducting the irradiation to the optode 110. The light travels for example over a mirror 107 of an optode holder 108. The measuring light going from the optode travels back over the same path.

Figure 2A:
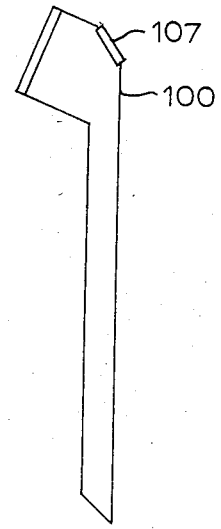
FIG. 2A is a view showing a modification of an element of the arrangement of FIG. 2.

An arrangement 1100 shown in FIG. 2A is a one-piece formation of the individual parts, namely the coupling surface 105, the light conductor 106, the mirror 107, and the optode holder 108. It can be produced as an integral element and inserted into the carrier body 10 provided with the respective passages.

FIG. 3 shows an arrangement for measuring diffusing particles in which conductors a, b, c are provided on the carrier body. It is thereby possible to arrange color detecting light diodes 120 and photoreceivers 121 in the carrier body, so that they are supplied by the conductors a, b and their signals are taken via the conductors b, c. Depending upon the available space, arrangements of FIG. 3A or FIG. 3B are utilized.

In this case, arrangement 1200 or 1210 are composed of units which include a light diode 120, a mirror 122, a photoreceiver 121, and an optode holder 123, and arranged in the carrier body 10.

It will be understood that each of the elements described above, or two or more together, may also find a useful application in other types of constructions differing from the types described above.

While the invention has been illustrated and described as embodied in an arrangement for measuring diffusing particles, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An arrangement for measuring diffusing particles comprising a plurality of material limited indicator chambers permeable to the particles to be measured and provided with optical fluorescent indicators which are optically changeable by the particles for simultaneously measuring several physical parameters and/or several types of particles, said indicator chambers being formed as optodes; a carrier body having a surface arranged to lie on a lid under the latter and provided in this surface with depressions in which said optodes are arranged; at least one monochromatic irradiation source arranged to irradiate said optodes; and a light measuring device arranged to measure light going out of the optodes and its change.

2. An arrangement as defined in claim 1, wherein said carrier body has an edge provided with at least one coupling surface; and further comprising light conductors provided inside said carrier body and guiding light from said at least one coupling surface to said indicator chambers.

3. An arrangement as defined in claim 1, wherein said indicator chambers are arranged in said depressions of said carrier body at such a location that measurements through the eyelid can be performed.

4. An arrangement as defined in claim 1, wherein said light measuring device includes a radiation receiver, said monochromatic radiation source and said radiation receiver being arranged in said carrier body, so that the irradiation of the optodes and the measurement of the radiation change is performed directly in said carrier body.

5. An arrangement as defined in claim 1; and further comprising means for optical disengagement formed by layers arranged at a side facing toward the retina.

6. An arrangement as defined in claim 5, wherein said layers of said optical disengagement means are formed as reflecting layers.

7. An arrangement as defined in claim 5, wherein said layers of said optical disengagement means are formed as absorbing layers.

8. An arrangement as defined in claim 1, wherein said light measuring device is arranged inside said carrier body.

9. An arrangement as defined in claim 1, wherein said carrier body has a recess, said light conducting devices being formed as one-piece elements received in said recess.

10. An arrangement as defined in claim 8, wherein said carrier body has a recess, said light measuring device being arranged in said recess of said carrier body.

* * * * *